US008157848B2

(12) United States Patent
Zhang et al.

(10) Patent No.: US 8,157,848 B2

(45) Date of Patent: Apr. 17, 2012

(54) SYSTEM FOR CHARACTERIZING PATIENT TISSUE IMPEDANCE FOR MONITORING AND TREATMENT

(75) Inventors: Hongxuan Zhang, Schaumburg, IL (US); Detlef W. Koertge, Carpentersville, IL (US); Dennis Steibel, Jr., Lake Zurich, IL (US); Harold James Wade, Rockford, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 530 days.

(21) Appl. No.: 12/356,901

(22) Filed: Jan. 21, 2009

(65) Prior Publication Data

US 2009/0198300 A1 Aug. 6, 2009

Related U.S. Application Data

(60) Provisional application No. 61/025,423, filed on Feb. 1, 2008.

(51) Int. Cl.
*A61N 1/00* (2006.01)

(52) U.S. Cl. .............................................. 607/1; 607/28

(58) Field of Classification Search ................ 607/1, 28; 600/506, 377

See application file for complete search history.

(56) References Cited

U.S. PATENT DOCUMENTS 4,321,932 A 3/1982 Francis
4,577,639 A 3/1986 Simon et al.
4,917,099 A 4/1990 Stice
5,002,064 A 3/1991 Allain et al.
5,309,917 A 5/1994 Wang et al.
5,448,997 A 9/1995 Kruse et al.
5,542,430 A 8/1996 Farrugia et al.
5,562,721 A 10/1996 Marchlinski et al.
5,788,644 A 8/1998 Donehoo et al.
5,879,308 A 3/1999 Räsänen
5,921,939 A 7/1999 Danielsson et al.
6,015,389 A 1/2000 Brown
6,070,100 A * 5/2000 Bakels et al. .................... 607/9
6,516,218 B1 2/2003 Cheng et al.
6,522,924 B1 2/2003 Meier (Continued)

OTHER PUBLICATIONS

Ali A. Mehdirad, Erich C. Stohr, Charles J. Love, Steven D. Nelson, and Stephen F. Schaal, "Implantable Defibrillators Impedance Measurement Using Pacing Pulses Versus Shock Delivery with Intact and Modified High Voltage Lead System", Pacing and Clinical Electrophysiology, vol. 22, No. 3, p. 437-441, 1999.

(Continued)

*Primary Examiner* — Niketa Patel
*Assistant Examiner* — Alyssa M Alter
(74) *Attorney, Agent, or Firm* — Alexander J Burke

(57) ABSTRACT

A system provides early prediction of heart tissue malfunction and electrophysiological pathology by determining anatomical tissue impedance characteristics for use in medical patient monitoring and treatment decision making. At least one repository of data indicates multiple predetermined expected impedance value ranges for corresponding multiple impedance measurements taken at multiple particular different sites of at least one anatomical organ. An impedance measurement processor automatically determines whether multiple measured impedance values taken at multiple particular different sites of an anatomical organ using an invasive catheter are within corresponding multiple predetermined expected impedance value ranges derived from the at least one repository. An output processor automatically communicates data comprising at least one message to a destination. The at least one message includes data indicating whether the multiple measured impedance values taken at the multiple particular different sites of the anatomical organ are within the corresponding multiple predetermined expected impedance value ranges.

16 Claims, 6 Drawing Sheets

309
305
303
R2
R3
R1
R4
High
Low

Catheter in Right atrium
(with atrial fibrillation point)

Basket catheter

Impedance measuring and mapping

U.S. PATENT DOCUMENTS

| | | | |
|---|---|---|---|
| 6,839,587 | B2 | 1/2005 | Yonce |
| 6,907,290 | B2 | 6/2005 | Legay |
| 6,974,420 | B2 | 12/2005 | Kaiser et al. |
| 7,062,326 | B2 | 6/2006 | Huvelle et al. |
| 7,200,440 | B2 | 4/2007 | Kim et al. |
| 7,228,173 | B2 | 6/2007 | Cazares |
| 7,245,961 | B2 | 7/2007 | Blakley et al. |
| 2009/0157337 | A1 | 6/2009 | Zhang et al. |

OTHER PUBLICATIONS

Gerry Kaye, Deborah Edgar, Telal Mudawi, Michael Lippert and Gerald Czygan, “Can transventricular intracardiac impedance measurement discriminate haemodynamically unstable ventricular arrhythmias in human?”, Europace, 2007, vol. 9, No. 2, p. 122-126.

Firatduru, Rogerluechinger, Christophscharf, and Corinnabrunckhorst,“Automatic Impedance Monitoring and Patient Alert Feature in Implantable Cardioverter Defibrillators: Being Alert for the Unexpected!” Journal of Cardiovascular Electrophysiology, vol. 16, Issue 4, p. 444-448, 2005.

Tamir Wolf, Lior Gepstein, Gal Hayam, Asaph Zaretzky, Rona Shofty, Dina Kirshenbaum, Gideon Uretzky, Uri Oron, and Shlomo A. Ben-Haim, “Three-dimensional endocardial impedance mapping: a new approach for myocardial infarction assessment”, Am J Physiol Heart Circ Physiol, vol. 280, No. 1, p. 179-188, 2001.

* cited by examiner

SYSTEM FOR CHARACTERIZING PATIENT TISSUE IMPEDANCE FOR MONITORING AND TREATMENT

This is a non-provisional application of provisional application Ser. No. 61/025,423 filed Feb. 1, 2008, by H. Zhang et al.

FIELD OF THE INVENTION

This invention concerns a system for determining anatomical tissue impedance characteristics of multiple different sites of an anatomical organ using an invasive catheter for use in medical patient monitoring and treatment decision making.

BACKGROUND OF THE INVENTION

Cardiovascular disease is a major cause of fatalities. Cardiac electrophysiological (EP) signals are used to diagnose and characterize patient electrophysiological pathology, such as atrial fibrillation and myocardial ischemia (MI). Usually, surface electrocardiograph (ECG) signal and intra-cardiac EP signal analysis based on waveform morphology and time domain parameters is employed for cardiac arrhythmia detection and characterization, involving determining P wave morphology changes, R-R wave time intervals and analyzing heart rate variability, for example. However, there is a lack of a precise and reliable method for categorizing electrophysiological characteristics based upon heart tissue analysis and diagnosis.

Some known research studies describe tissue impedance based analysis, such as for heart evaluation for use in a heart tissue ablation procedure and cardiac arrhythmia discrimination. However, known tissue impedance analysis methods typically focus on calculation of a single EP impedance characteristic based on an external stimulation pulse. Known methods suffer from introduction of electrical noise into EP signals as well as from current and/or voltage leakage that may impair patient safety. Known systems typically employ an external energy source to induce stimulation of a heart and derive myocardial tissue impedance and tissue electrophysiological characteristics. However, this stimulation may cause change to heart tissue electrophysiological characteristics, potentially resulting in patient safety impairment. Precision and reliability of impedance measurement and analysis in known systems is affected by dynamic variation of external stimulation signals and may vary from patient to patient. Additionally, known corresponding clinical methods fail to address multi-channel intra-cardiac impedance mapping and pattern analysis for a cardiac tissue and heart circulation system.

Known current signal processing systems use intra-cardiac electrograms to analyze cardiac arrhythmias, such as Atrial Fibrillation (AF) and Ventricular Fibrillation (VF) but lack diagnosis accuracy and reliability. Although anatomical structure and geometry models may be used by some known medical devices, these models lack precision and reliability in localizing malfunctioning tissue, determining heart arrhythmia severity and life-threatening event timing, especially of a multi-site reentrant mechanism cardiac function. Intra-cardiac electrophysiological signals (ICEG) are used in analyzing and characterizing cardiac pathology and arrhythmias. However, known medical devices fail to characterize tissue status or indicate an underlying cause of an arrhythmia event. A system according to invention principles addresses these deficiencies and associated problems.

SUMMARY OF THE INVENTION

A system provides early prediction of heart tissue malfunction and electrophysiological pathology and real-time intra-cardiac impedance mapping with precise pathological tissue localization, determination of cardiac arrhythmia severity and enables prediction of life-threatening events by passively measuring and diagnosing patient intra-cardiac tissue impedance using invasive heart catheters (such as EP diagnostic and ablation catheters). A system determines anatomical tissue impedance characteristics for use in medical patient monitoring and treatment decision making. At least one repository of data indicates multiple predetermined expected impedance value ranges for corresponding multiple impedance measurements taken at multiple particular different sites of at least one anatomical organ. An impedance measurement processor automatically determines whether multiple measured impedance values taken at multiple particular different sites of an anatomical organ using an invasive catheter are within corresponding multiple predetermined expected impedance value ranges derived from the at least one repository. An output processor automatically communicates data comprising at least one message to a destination. The at least one message includes data indicating whether the multiple measured impedance values taken at the multiple particular different sites of the anatomical organ are within the corresponding multiple predetermined expected impedance value ranges.

DETAILED DESCRIPTION OF THE INVENTION

Figure 1:
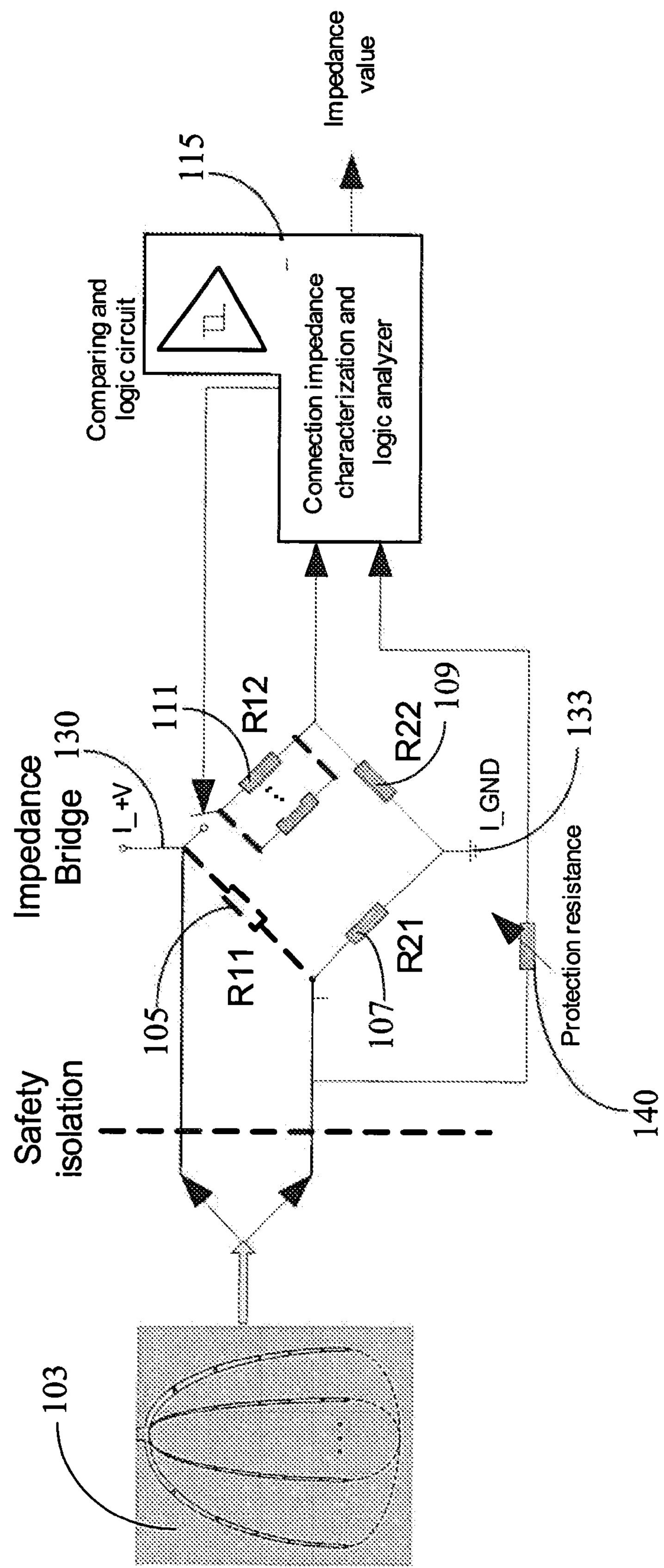
FIG. 1 shows an automatic controllable balance bridge for intra-cardiac tissue measurement, analysis and characterization, according to invention principles.

A system provides early prediction of heart tissue malfunction and electrophysiological pathology that is especially useful in non-symptomatic cardiac arrhythmias and prediction of secondary injury in a heart and circulatory system. The system provides a more efficient, accurate and reliable method for real-time accurate intra-cardiac impedance mapping with precise pathological tissue localization and cardiac arrhythmia severity characterization. The system in one embodiment employs a controllable impedance bridge to passively measure and diagnose patient intra-cardiac tissue impedance using heart catheters (such as EP diagnostic and ablation catheters) and improve safety of myocardial impedance measurement and diagnosis. This advantageously uses a patient's own cardiac signals and electrophysiological activities eliminating use of an active current of a stimulation signal and associated safety risk and additional procedure complexity. The system is usable for investigation and characterization of myocardial arrhythmias and pathology status, including: 1) Impedance bridge based myocardial tissue impedance measurement and characterization; 2) Electrophysiological impedance mapping and pattern analysis based myocardial function and pathology diagnosis and quantification for heart tissue and an intra-cardiac circulation system.

The system electrode impedance bridge employs both unipolar and bipolar modes and provides a multi-dimensional resistance and impedance map for patient health and real-time heart function monitoring and disease diagnosis. Furthermore, the system automatic real time electrophysiological impedance measurement and analysis reduces cost and complexity of medical diagnosis and treatment, and improves sensitivity, stability and reliability of a corresponding clinical application. The automatic system is used to provide doctors with a straightforward, precise and reliable analysis in contrast to known cardiac electrograms (such as ECG and ICEG) signal-based monitoring and analysis which requires extensive expertise and clinical experience for accurate pathology interpretation and proper cardiac rhythm management. The passive balance bridge based impedance matching and measurement system analyzes and characterizes tissue EP impedance between two leads or sensors without introducing additional electrical current, voltage or energy to improve EP signal quality (high signal to noise ratio) and patient safety. The system quantifies electrophysiological response signals as well as cardiac tissue. The electrophysiological characteristic analysis is usable for different kinds of cardiac arrhythmias, such as AF, VF, MI arrhythmias, for example. Tissue impedance is an intrinsic electrophysiological characteristic of heart tissue that provides accurate and reliable information.

Cardiac tissue defects and associated impedance changes typically occur earlier than indications in an electrophysiological waveform. This enables the system to advantageously provide early defect detection, real-time monitoring, and more sensitive indications to a doctor of heart tissue and intra-cardiac circulation defects. The system implements multi-channel impedance mapping using a basket catheter, for example, to support real time electrophysiological impedance mapping based myocardial function and pathology diagnosis and quantification. The system real time tissue impedance monitoring is performed with milli-second response time and provides tissue impedances within an individual heart beat or impedances averaged over multiple heart beats as well as time based averaged impedances. The system does not require additional medical procedures or complexity.

A processor as used herein is a device for executing stored machine-readable instructions for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a controller or microprocessor, for example. A processor may be electrically coupled with any other processor enabling interaction and/or communication there-between. A processor comprising executable instructions may be electrically coupled by being within stored executable instruction enabling interaction and/or communication with executable instructions comprising another processor. A user interface processor or generator is a known element comprising electronic circuitry or software or a combination of both for generating display images or portions thereof. A user interface comprises one or more display images enabling user interaction with a processor or other device.

An executable application comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a user interface processor and enabling user interaction with a processor or other device and associated data acquisition and processing functions.

The UI also includes an executable procedure or executable application. The executable procedure or executable application conditions the user interface processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

FIG. 1 shows automatic controllable balance impedance bridge 10 for passive intra-cardiac tissue measurement, analysis and characterization. Typically, average measured intra-cardiac patient tissue impedance is around 75 ohms and fluctuates between 35 and 150 ohms during a heart beat cycle. Tissue analysis comprising real time substantially instantaneous tissue impedance monitoring and characterization using an impedance bridge reveals valuable data. Impedance measurements are also mapped to predetermined ranges to establish intra-cardiac electrophysiological characteristics. In impedance bridge 10, R11 (105) is an intra-cardiac local tissue impedance comprising one of multiple different impedances successively measured between individual pairs of contact elements of one of the individual branches of basket catheter 103. Basket catheter 103 or another type of invasive catheter is inserted in a heart chamber, other organ, or anatomical portion so that catheter electrical contacts rest against tissue walls. R11 (105) may also comprise an impedance measured between a pair of contact elements of different branches of basket catheter 103. R11 (105) is measured through a safety isolation component such as a transformer with sufficient primary to secondary clearance and creepage distances or an opto-isolator, for example. R11 (105) forms one balance impedance in the impedance bridge including R12 (111), R21 (107), and R22 (109) balancing impedance components, which are individually tunable and adjustable for different situations and patients (including different patient ages, gender, weight, height etc.).

In system 10, typically the impedances are measured between Isolated power (I_+V 130) and isolated ground (I_GND 133) for patient safety in case of high voltage fibrillation, for example. The system automatically tunes and adjusts bridge impedance and determines an impedance range of R11 (105) in response to control signals provided by impedance measurement processor 115. In one embodiment, if the determined impedance range of R11 (105) lies outside of a normal value range, and is higher than 10 kOhms, for example, impedance measurement processor 115 outputs a message signal indicating a large intra-cardiac impedance. If the determined impedance range of R11 (105) lies within a normal range such as between 35 and 150 Ohms for one type of impedance measurement, impedance bridge 10 and impedance measurement processor 115 does not output a warning message signal. However, if the determined impedance range of R11 (105) is determined to be greater than a predetermined normal range associated with the type of organ, patient and type of impedance being measured and the particular time within the heart cycle the measurement is made, impedance measurement processor 115 sends an alert message signal. Impedance measurement processor 115 also characterizes the impedance based on range and in the light of multiple different impedances measured and maps the impedance in the light of the other impedances to a diagnostic message or treatment related message sent to a user to indicate in substantially real-time, suggested actions or tests to be performed and medications and treatments to be taken.

Impedance measurement processor 115 controls the impedance matching circuit including R11 (105), R12 (111), R21 (107), and R22 (109) (for EP impedance measurement) and receives intra-cardiac electrogram signals via protective impedance 140 (e.g., a resistance). Impedance 140 provides additional protection of a patient. Impedance measurement processor 115 conditions received intra-cardiac electrogram signals by amplifying, filtering, and digitizing the signals. Impedance measurement processor 115 directs the impedance bridge of system 10 to characterize R11 (105) by comparing R11 (105) with predetermined impedance ranges associated with predetermined diagnostic and treatment criteria. Processor 115 controls analysis of an array of determined data including R11 (105) of an organ, other impedances of the organ measured using an EP catheter, patient medical history and demographic data (age, gender, height, weight) and received intra-cardiac electrogram signals to determine diagnostic or treatment suggestions to provide to a user. Further, the impedance bridge advantageously involves negligible current and once the bridge circuit is in balance, the current is nearly zero.

Patient impedance, particularly intra-cardiac tissue impedance, has an intrinsic relationship with cardiac diseases such as myocardial ischemia evidenced by increasing local cardiac electrophysiological impedance. Cardiac arrhythmias are typically a result of tissue abnormality. For example, if there is a reentrant mechanism occurring within a heart atrium, electrical excitation conduction may be affected resulting in partial electrophysiological blockage and change in impedance characteristics of local tissue within the atrium. So local tissue impedance monitoring, measurement, and characterization enables detection and quantification of heart arrhythmia.

Figure 2:
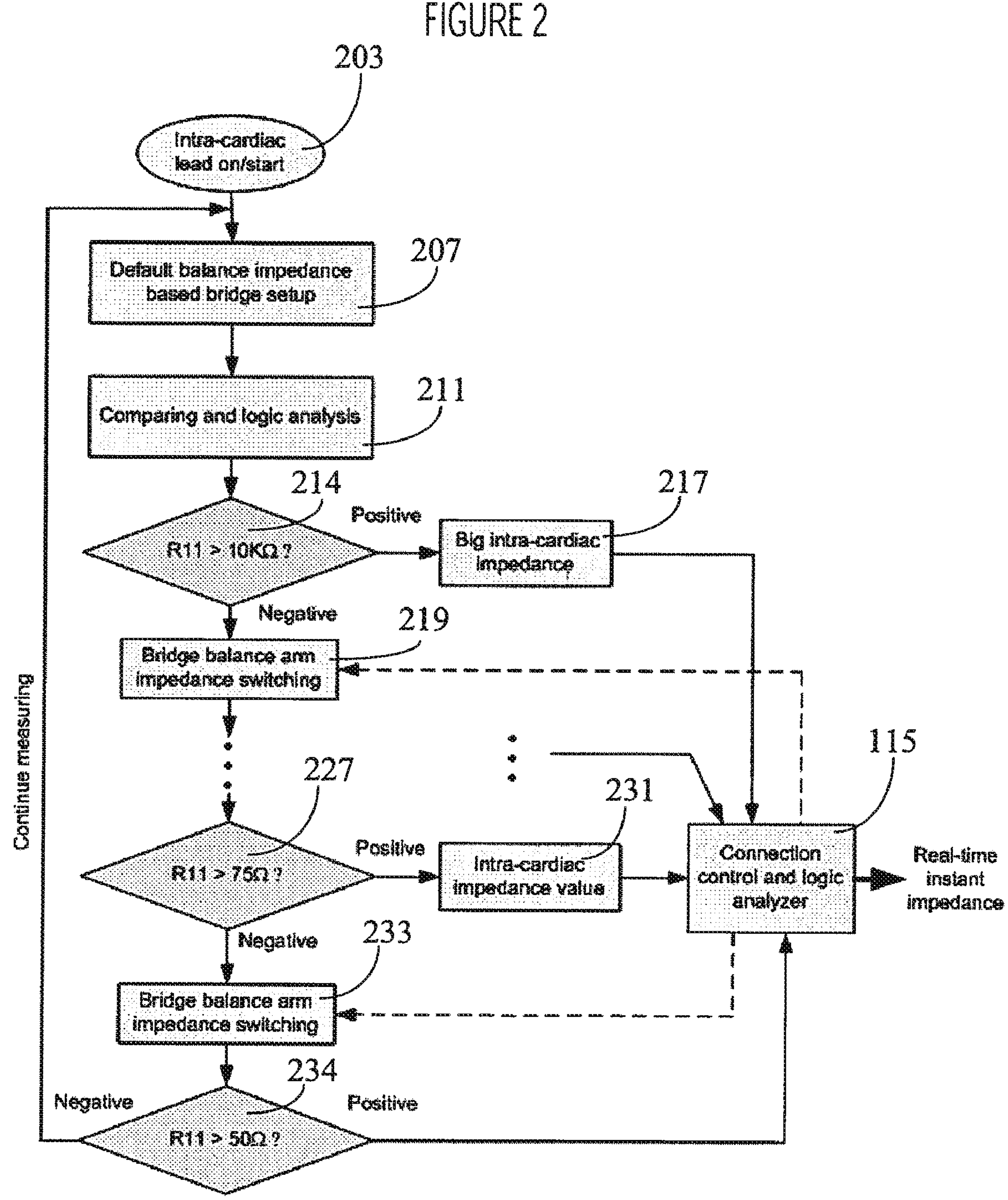
FIG. 2 shows a flowchart of a process performed by a system for determining anatomical tissue impedance characteristics for use in medical patient monitoring and treatment decision making, according to invention principles.

FIG. 2 shows a flowchart of a process performed by a system for determining anatomical tissue (e.g., intra-cardiac) impedance characteristics for use in medical patient monitoring and treatment decision making. The process employs multi-range impedance matching and balancing to determine accurate local cardiac tissue impedances. Impedance measurement processor 115 (FIG. 1) controls the impedance bridge balance switching steps and performs automatic continuous and substantially instantaneous impedance measurement as well as mapping and characterization of tissue electrophysiological activities to diagnostic and treatment characteristics. A time based impedance pattern is derived by synchronizing ECG or ICEG electrograms with R wave gating for dynamic cardiac tissue impedance comparison at particular times (for example, normal and atrial fibrillation (AF) stage) or depolarization and repolarization stages. The system also supports variation analysis and characterization.

In the FIG. 2 process, intra-cardiac tissue impedance is matched within predetermined range values in ranges between 10 KOhms and 50 Ohms (the impedance ranges are automatically tuned and may be set by a patient monitoring device). The process compares and matches impedances with predetermined ranges and provides a substantially instantaneous intra-cardiac impedance value within a time period of milli-seconds.

Following power-on in step 203, impedance measurement processor 115 in step 207 controls the impedance balance arm and initially selects a default R12 (111) value of 10 kOhms, for example. If the impedance bridge comparison in step 211 provides a Positive output value in step 214 indicating intra-cardiac tissue impedance exceeds 10 kOhms (i.e., an abnormal value), the intra-cardiac tissue impedance is provided in step 217 to impedance measurement processor 115. Otherwise, if the output of the bridge is Negative, impedance measurement processor 115 in step 219 automatically successively switches impedance R12 (111) to compare R11 (105) with multiple different range values between 10 kOhms and 75 Ohms. For example, if the impedance bridge comparison provides a Positive output value in step 227, data is provided in step 231 to impedance measurement processor 115 that indicates R11 (105) is between 75 Ohms and a previous threshold range limit higher value (e.g., 100 Ohms). If the impedance bridge comparison provides a Negative output value in step 227 indicating R11 (105) is less than 75 Ohms, impedance measurement processor 115 in step 233 automatically successively switches impedance R12 (111) to compare R11 (105) with 50 Ohms. If the impedance bridge comparison provides a Negative output value in step 234 indicating R11 (105) is less than 50 Ohms further range selection iteration is performed from step 207 with new ranges selected by processor 115. If the impedance bridge comparison provides a Positive output value in step 234, data is provided to processor 115 that indicates R11 (105) is between 75 Ohms and 50 Ohms. The system automatically measures and characterizes an intra-cardiac tissue impedance range. The impedance verification and range testing may be implemented between signals (including between a signal and patient reference), and between a signal and GND (instrumentation isolated ground reference).

Processor 115 performs additional statistical analysis and evaluation comprising solid pattern analysis and characterization of an intra-cardiac dynamic impedance. Processor 115 determines, for example, dynamic intra-cardiac impedance of tissue at a particular point of a heart beat cycle within a first heart beat is A±Δa and dynamic intra-cardiac impedance of the tissue at a corresponding particular point of a heart beat cycle in a second heart beat is B±Δb. Thereby a user is able to compare average values for tissue impedance for the same heart electrophysiological stages. Sometimes, if A and B are similar, the measurement deviation is a significant index of diagnostic value. For arrhythmia evaluation and disease characterization, a statistical significance hypothesis test and analysis methods are employed for quantification of impedance changes such as a T test and Z test (which compare between two means to suggest whether samples come from the same population), for example.

The system advantageously uses multi-channel cardiac tissue impedance measurement using a basket catheter, for example, to provide real time cardiac tissue mapping and characterization of a substantial region of tissue. In comparison, a single channel cardiac tissue impedance measurement is limited to monitoring an EP index of a local small tissue region. The system multi-channel heart tissue analysis advantageously provides early detection and diagnosis of cardiac arrhythmia, such as myocardial ischemia and infarction. The system also provides accurate real-time intra-cardiac mapping (of heart, chambers and circulation system) with precise pathological tissue localization (in 2D and 3D position) in the heart and synchronized within a heart cycle.

Figure 3:
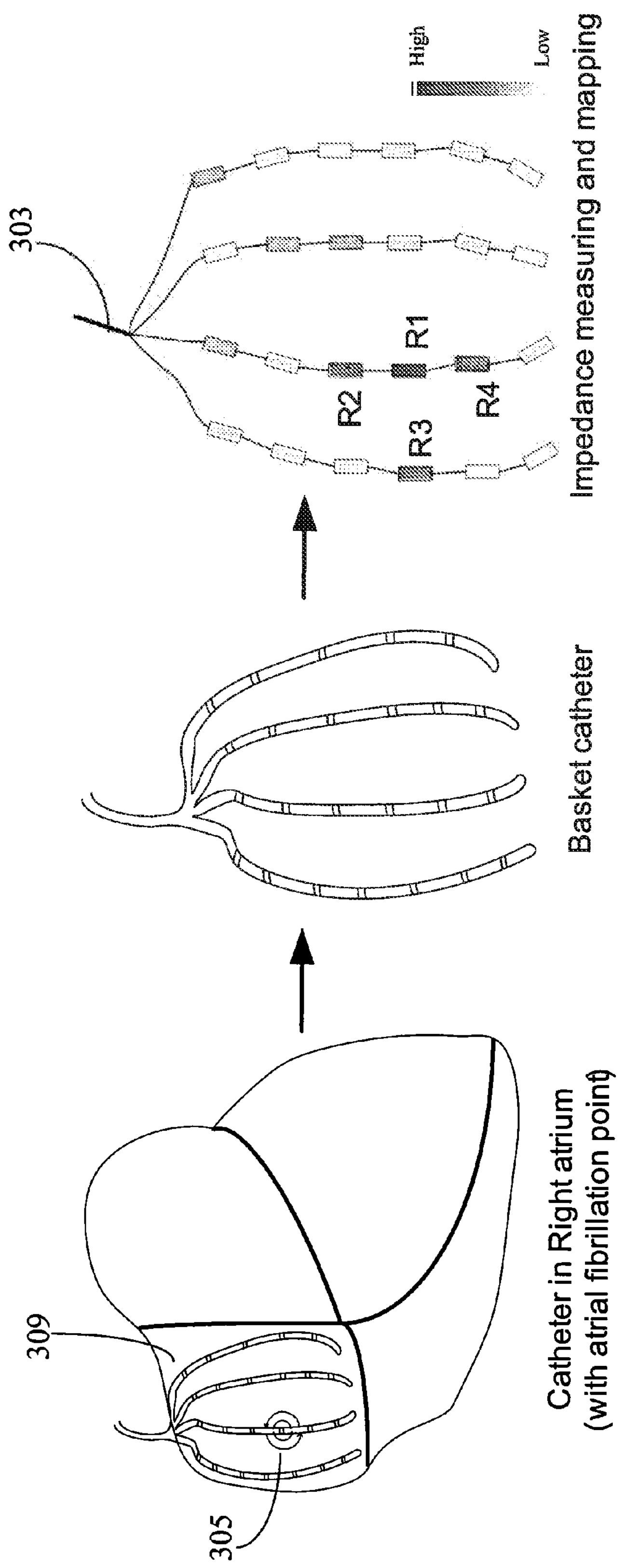
FIG. 3 shows use of a basket EP catheter for multi-channel intra-cardiac impedance mapping and anatomical tissue impedance characteristic determination for use in medical patient monitoring and treatment decision making, according to invention principles.
Figure 5:
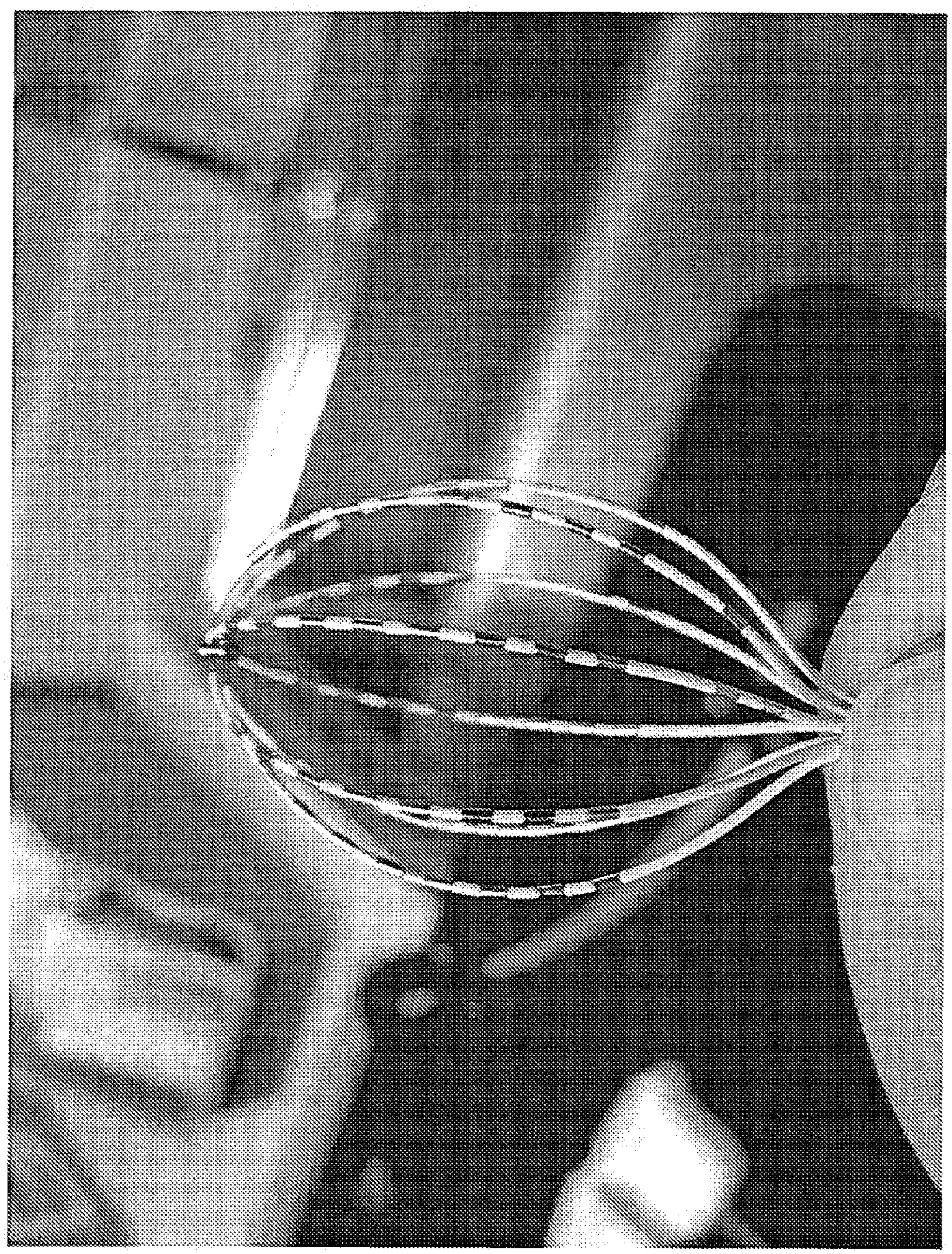
FIG. 5 shows a basket EP catheter used in multi-channel intra-cardiac impedance mapping and anatomical tissue impedance characteristic determination, according to invention principles.

FIG. 3 shows use of a basket EP catheter for multi-channel intra-cardiac impedance mapping and anatomical tissue impedance characteristic determination for use in medical patient monitoring and treatment decision making. FIG. 5 shows a basket EP catheter used in multi-channel intra-cardiac impedance mapping and anatomical tissue impedance characteristic determination. Basket catheter 303 (FIG. 3) measures individual tissue impedances along individual catheter branches (including R1, R2, R3 and R4) and is inserted in right atrial chamber 309 to provide impedance mapping and diagnosis. Individual measured tissue impedances, e.g., R1, R2, R3 and R4 are correlated by mapping by processor 115 (FIG. 1) with an arrhythmia and tissue abnormality indicated by electrophysiological characteristics using a look-up mapping table stored in processor 115, for example. In operation, during right atrial chamber 309 monitoring, a reentrant rotor is emerging and potentially an AF arrhythmia is occurring. Impedance measurement processor 115 analyzes local EP impedances and determines R1, R2, R3 and R4 have changed because of an abnormal AF rotor and R1 is the center of the arrhythmia (and a high severity pathological tissue region).

The system takes advantage of the fact a cardiac arrhythmia event typically changes a normal electrophysiological conducting pathway. For example, during AF or MI cases, cardiac tissue conduction is often partially blocked and modified, which, in turn, results in a higher impedance value of the corresponding arrhythmic tissue and an increased impedance value variance. Impedance measurement processor 115 identifies a cardiac arrhythmia region 305 by mapping of the impedance region comprising R1, R2, R3 and R4 to region 305. Processor 115 also localizes the tissue region having the highest severity (i.e., the center) of the arrhythmia to the particular location of impedance R1. Data indicating the region of highest severity is provided by processor 115 for use by a physician in determining a region for ablation treatment, for example. Processor 115 processes tissue impedance values to predict secondary injury and provide diagnostic and treatment candidate suggestions using a predetermined repository of information associating organ, impedance value patterns categorized by patient demographic data and corresponding diagnostic and treatment suggestions.

The system employs impedance mapping for heart function modeling and pathology localization and diagnosis using an intra-cardiac basket lead catheter for early detection and diagnosis of myocardial ischemia and infarction, for example. Typically, low blood flow affects tissue first, such as the functionality and working mechanism of the ion channel and this causes characteristic electrical changes to occur gradually, such as changes to tissue impedance. Eventually, the electrophysiological signals, such as ST segment signals are changed due to the mass ion channel blockage and abnormal function. Therefore, the system advantageously uses organ tissue electrical impedance characteristics to provide an early diagnosis and prediction of arrhythmias. Further, the system supports real time heart cycle synchronized monitoring and diagnosis of intra-cardiac tissue impedance at selectable heart stages. The system enables comparison of electrophysiological characteristics (e.g., impedance) for, a repolarization stage of different heart beats, a depolarization stage of different heart beats, a static stage of different heart beats and an average of a single heart beat or multiple heart beats.

Figure 4:
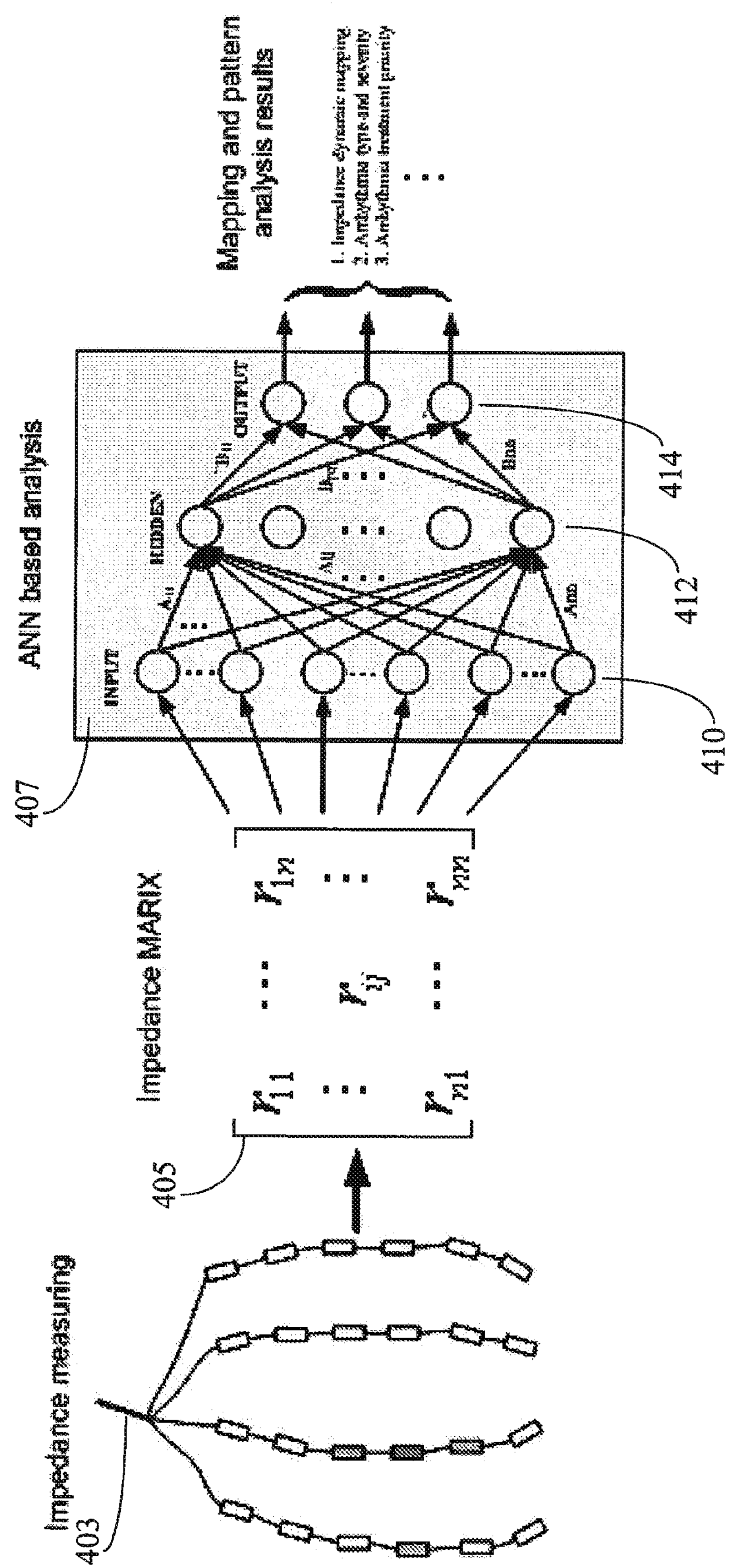
FIG. 4 shows use of a basket EP catheter for multi-channel ANN (Artificial Neural Network) based intra-cardiac tissue impedance mapping and anatomical tissue impedance characteristic determination for use in medical patient monitoring and treatment decision making, according to invention principles.

FIG. 4 shows use of a basket EP catheter for multi-channel ANN (Artificial Neural Network) based intra-cardiac tissue impedance mapping and anatomical tissue impedance characteristic determination for use in medical patient monitoring and treatment decision making. Chamber and heart tissue mapping and electrophysiological pattern analysis are relatively complex operations compared with use of a single EP catheter impedance measurement. In one embodiment, the system uses and combines multi-channel tissue impedances and employs a three layer artificial neural network (ANN) to calculate an index and value categorizing severity and treatment urgency. FIG. 4 shows a 3-layer ANN based intra-cardiac impedance analysis system. The system employs an ANN unit that is trained for versatile diagnosis and determination of characteristics including arrhythmia type, severity, treatment priority categorization. The ANN based impedance analysis is extended to use additional patient information including, electrophysiological data (ECG and ICEG signals), patient history data, vital signs data, hemodynamic data, and data derived by analysis and calculation (using frequency analysis, for example). Thereby the system determines characteristics of patient pathologies and cardiac malfunctions.

In the system of FIG. 4 which is incorporated in impedance processor 115 (FIG. 1), impedances measured using intra-cardiac catheter 403 are incorporated in matrix 405 and processed using ANN (Artificial Neural Network) processor 407 by mapping intra-cardiac tissue impedances to candidate diagnosis and treatment suggestions. The ANN unit 407 structure comprises 3 layers, an input layer 410, hidden layer 412 and output layer 414. ANN unit $A_{ij}$ weights are applied between input layer 410 and hidden layer 412 components of the ANN computation and $B_{pq}$ weights are applied between hidden layer 412 and calculation index components 414 of the ANN computation. The $A_{ij}$ weights and $B_{pq}$ weights are adaptively adjusted and tuned using a training data set. ANN calculation and decision processor 407 incorporates a self-learning function that processes new input data to increase the accuracy and precision of calculated results using impedance matrix 405. The system transfers multi-channel impedance measurements from basket catheter 403 to impedance matrix 405. Matrix 405 may comprise a three dimensional (3D) matrix in one embodiment. ANN processor 407 analyzes values in impedance matrix 405 by performing electrophysiological pattern analysis to identify pertinent impedance patterns in a heart chamber, for example, and mapping determined impedance patterns to a candidate diagnosis or treatment decision. ANN processor 407 performs impedance dynamic mapping to localize a tissue impairment within an organ and determine time of occurrence within a heart cycle. Processor 407 also identifies arrhythmia type (e.g., AF, MI, VT, VF), severity of arrhythmia treatment and urgency level and is usable for automatic heart condition detection, diagnosis, warning and treatment. In addition, processor 407 adaptively recognizes data and mapping variations resulting from beating heart and muscle movement. Further processor 407 performs statistical analysis to construct a threshold used to detect tissue impairment and diagnose and predict cardiac arrhythmia and pathology.

Following a training phase with a training data set, ANN processor 407 processes values in impedance matrix 405 to provide a 3D cardiac electrophysiological function mapping to data indicating an Arrhythmia type, Arrhythmia severity, candidate treatment suggestions, localized tissue impairment information identifying the cardiac arrhythmia position, pathology conducting sequence, abnormal tissue area and focus of the disorder and irregularity, for example. In the other embodiments processor 407 may comprise a Fuzzy-Logic processor or expert system, for example.

Figure 6:
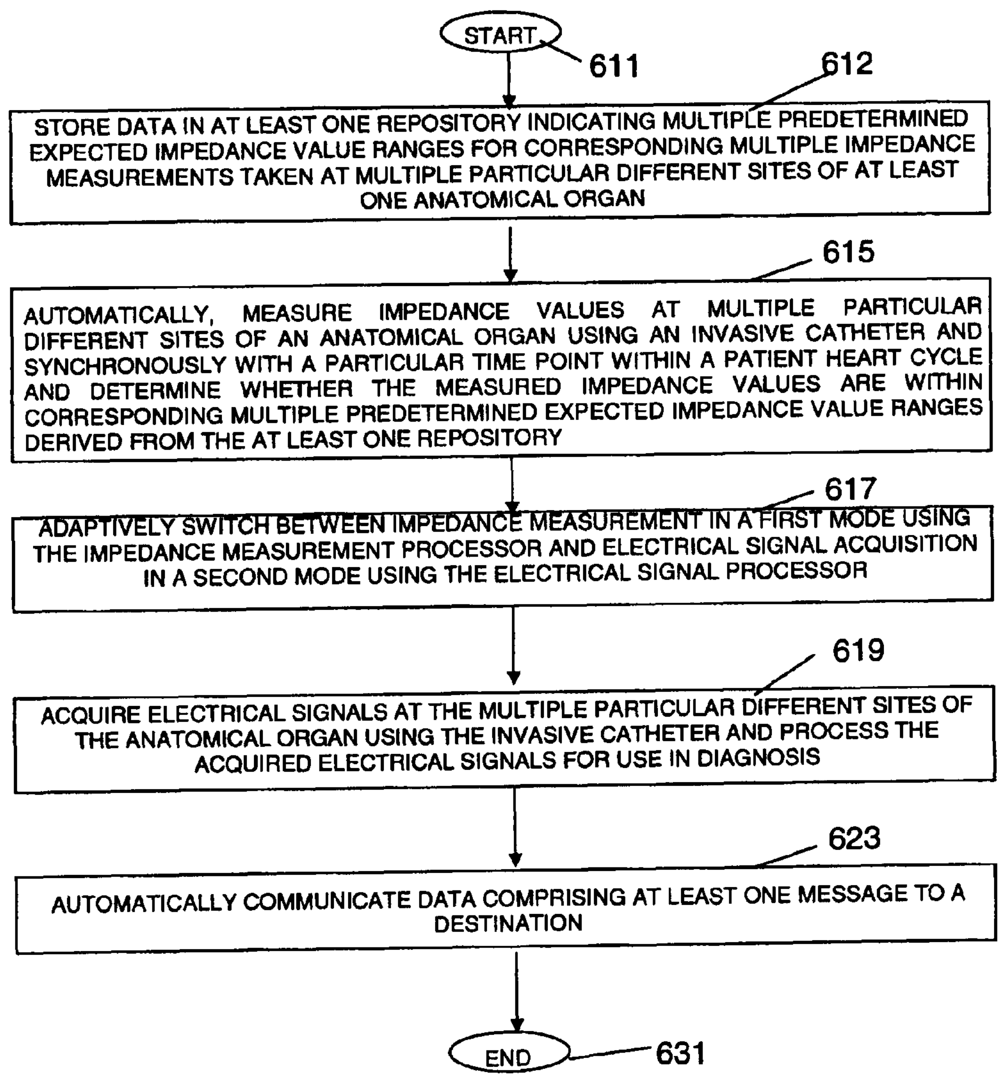
FIG. 6 shows a flowchart of a process performed by a system for determining anatomical tissue impedance characteristics for medical patient monitoring and treatment decision making, according to invention principles.

FIG. 6 shows a flowchart of a process performed by a system for determining anatomical tissue impedance characteristics for medical patient monitoring and treatment decision making. In Step 612, following the start at step 611, impedance measurement processor 115 (FIG. 1) stores in at least one repository within processor 115, data comprising multiple predetermined expected impedance value ranges and corresponding previously performed impedance measurement values taken at multiple particular different sites of an anatomical organ of a particular patient. Data stored in the at least one repository also indicates multiple predetermined expected impedance value ranges and corresponding different treatment decision related information for corresponding multiple impedance measurements taken at a single site of an anatomical organ at multiple different time points within a patient heart cycle. The multiple predetermined impedance value ranges include one or more of, (a) a value range indicating tissue ablation is not recommended, (b) a value range indicating tissue ablation may be recommended, (c) a value range indicating a first treatment may be recommended and (d) a value range indicating a second different treatment may be recommended. In one embodiment, an impedance value range of 50 Ohms to 1 K Ohm is deemed a normal range.

In step 615, impedance measurement processor 115 automatically determines whether differences between, measured impedance values taken at multiple particular different sites of the anatomical organ of the particular patient and the previously performed impedance measurement values, exceed a predetermined threshold. Impedance measurement processor 115 also automatically determines whether multiple measured impedance values taken at multiple particular different sites of the anatomical organ using an invasive catheter are within corresponding multiple predetermined expected impedance value ranges derived from the at least one repository. Further, in one embodiment impedance measurement processor 115 automatically, measures impedance values at multiple particular different sites of an anatomical organ using an invasive catheter and synchronously with a particular time point within a patient heart cycle. Processor 115 determines whether a synchronized impedance value measurement at a particular time point within the patient heart cycle is within a corresponding expected impedance value range associated with the particular time point within the patient heart cycle. In one example of operation, the organ comprises a heart and impedance measurement processor 115 determines whether multiple measured impedance values taken at multiple particular different sites within a heart chamber using an invasive multi-branch basket catheter are within corresponding multiple predetermined expected impedance value ranges derived from the at least one repository.

Impedance measurement processor 115 automatically successively determines the measured impedance values by successively altering a known impedance value in impedance bridge network 10 (FIG. 1). In one embodiment the measured impedance value and range is resistive and impedance measurement processor 115 applies DC voltage to the impedance bridge network in successively altering the known impedance value in the impedance bridge network to determine whether an impedance value lies in a particular range. In another embodiment the measured impedance value and range is reactive and comprises complex number values and impedance measurement processor 115 applies AC voltage to the impedance bridge network in successively altering a known impedance value in the impedance bridge network to determine whether an impedance value lies in a particular range.

A mode switch in processor 115 in step 617 adaptively switches between impedance measurement in a first mode using impedance measurement processor 115 and electrical signal acquisition in a second mode using the electrical signal processor. The electrical signal processor in processor 115 in step 619 acquires electrical signals at the multiple particular different sites of the anatomical organ using an invasive catheter and processes the acquired electrical signals for use in diagnosis. In step 623 an output processor in impedance processor 115 automatically communicates data comprising at least one message to a destination. The at least one message includes data representative of whether the differences between the multiple measured impedance values taken at multiple particular different sites of the anatomical organ of the particular patient and the previously performed impedance measurement values, exceed a predetermined threshold. The at least one message is also representative of whether the multiple measured impedance values taken at the multiple particular different sites of the anatomical organ are within the corresponding multiple predetermined expected impedance value ranges. The process of FIG. 6 terminates at step 631.

The systems and processes of FIGS. 1-6 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The system passively measures and diagnoses patient intra-cardiac tissue impedance impairments using heart catheters (such as EP diagnostic and ablation catheters) and improve safety of myocardial impedance measurement and diagnosis. Further, the processes and applications may, in alternative embodiments, be located on one or more (e.g., distributed) processing devices. Any of the functions and steps provided in FIGS. 1-6 may be implemented in hardware, software or a combination of both.

What is claimed is:

1. A system for determining anatomical tissue impedance characteristics for use in medical patient monitoring and treatment decision making, comprising:

at least one repository configured to storing data indicating a plurality of predetermined expected impedance value ranges for a corresponding plurality of impedance measurements taken at a plurality of particular different sites of at least one anatomical organ;

a substantially passive impedance measurement network operating exclusive of active current injection:

an impedance measurement processor using said impedance measurement network and configured to automatically, receiving signal data representing a plurality of measured impedance values taken at a plurality of particular different sites of an anatomical organ and determining whether the received plurality of measured impedance values are within a corresponding plurality of predetermined expected impedance value ranges derived from data in said at least one repository and are correlated with an anatomical abnormality; and an output processor configured to automatically communicating data comprising at least one message to a destination, said at least one message includes data indicating whether said received plurality of measured impedance values are within said corresponding plurality of predetermined expected impedance value ranges and indicate said abnormality.

2. A system according to claim 1, wherein said passive impedance measurement network is an impedance bridge network and said impedance measurement processor synchronizes measurements of said plurality of measured impedance values with a particular time point within a patient heart cycle.

3. A system according to claim 2, wherein said at least one repository of data indicates a plurality of predetermined expected impedance value ranges for a corresponding plurality of impedance measurements taken at a single site of an anatomical organ at a plurality of different time points within said patient heart cycle and said impedance measurement processor determines whether a synchronized impedance value measurement at a particular time point within said patient heart cycle is within a corresponding expected impedance value range associated with said particular time point within said patient heart cycle.

4. A system according to claim 1, wherein said at least one repository being configured to storing data indicating a plurality of different predetermined expected impedance value ranges and corresponding different treatment decision related information for a corresponding plurality of impedance measurements taken at a single site of an anatomical organ.

5. A system according to claim 4, wherein said plurality of predetermined impedance value ranges include at least one of, (a) a first value range indicating tissue ablation is not recommended and (b) a second value range indicating tissue ablation may be recommended.

6. A system according to claim 4, wherein said plurality of predetermined impedance value ranges include at least one of, (a) a first value range indicating a first treatment may be recommended and (b) a second value range indicating a second different treatment may be recommended.

7. A system according to claim 6, wherein an impedance value range of 50 Ohms to 1 K Ohm is deemed a normal range.

8. A system according to claim 1, wherein said organ comprises a heart and said impedance measurement processor determines whether a plurality of measured impedance values taken at a plurality of particular different sites within a heart chamber are within a corresponding plurality of predetermined expected impedance value ranges derived from said at least one repository.

9. A system according to claim 1, wherein said impedance measurement processor determines whether a plurality of measured impedance values taken at a plurality of particular different sites of an anatomical organ are within a corresponding plurality of predetermined expected impedance value ranges derived from said at least one repository.

10. A system according to claim 1, wherein said at least one repository being configured to storing data comprising a plurality of previously performed impedance measurements taken at a plurality of particular different sites of an anatomical organ of a particular patient and said impedance measurement processor automatically determines whether differences between, a plurality of measured impedance values taken at a plurality of particular different sites of the anatomical organ of said particular patient and said previously performed impedance measurements, exceed a predetermined threshold.

11. A system according to claim 1, including an impedance bridge network wherein said impedance measurement processor automatically successively determines said measured impedance values by successively altering a known impedance value in said impedance bridge network.

12. A system according to claim 11, wherein said measured impedance value and range is resistive and said impedance measurement processor applies DC voltage to said impedance bridge network in successively altering a known impedance value in said impedance bridge network to determine whether an impedance value lies in a particular range.

13. A system according to claim 11, wherein said measured impedance value and range is reactive and comprises complex number values and said impedance measurement processor applies AC voltage to said impedance bridge network in successively altering a known impedance value in said impedance bridge network to determine whether an impedance value lies in a particular range.

14. A system according to claim 1, including an electrical signal processor for acquiring electrical signals at said plurality of particular different sites of said anatomical organ and for processing the acquired electrical signals for use in diagnosis.

15. A system according to claim 14, including a mode switch for adaptively switching between impedance measurement in a first mode using said impedance measurement processor and electrical signal acquisition in a second mode using said electrical signal processor.

16. A method for determining anatomical tissue impedance characteristics for use in medical patient monitoring and treatment decision making, comprising the activities of:

storing data indicating a plurality of predetermined expected impedance value ranges for a corresponding plurality of impedance measurements taken at a plurality of particular different sites of at least one anatomical organ;

receiving signal data representing a plurality of measured impedance values taken at a plurality of particular different sites of an anatomical organ;

using a substantially passive impedance measurement network operating exclusive of active current injection in determining whether the received plurality of measured impedance values are within a corresponding plurality of predetermined expected impedance value ranges derived from the stored data and are correlated with an anatomical abnormality; and automatically communicating data comprising at least one message to a destination, said at least one message including data indicating whether said received plurality of measured impedance values are within said corresponding plurality of predetermined expected impedance value ranges and indicate said abnormality.

* * * * *